US011273279B2

(12) United States Patent
Grashow

(10) Patent No.: US 11,273,279 B2
(45) Date of Patent: Mar. 15, 2022

(54) MAGNETIC ANTI-CRUSH FEATURE FOR CONDUIT

(71) Applicant: KONINKLIJKE PHILIPS N.V., Eindhoven (NL)

(72) Inventor: Jonathan Sayer Grashow, Pittsburgh, PA (US)

(73) Assignee: Koninklijke Philips N.V., Eindhoven (NL)

(*) Notice: Subject to any disclaimer, the term of this patent is extended or adjusted under 35 U.S.C. 154(b) by 347 days.

(21) Appl. No.: 16/339,174

(22) PCT Filed: Sep. 29, 2017

(86) PCT No.: PCT/IB2017/056005
§ 371 (c)(1),
(2) Date: Apr. 3, 2019

(87) PCT Pub. No.: WO2018/065867
PCT Pub. Date: Apr. 12, 2018

(65) Prior Publication Data
US 2019/0224438 A1    Jul. 25, 2019

Related U.S. Application Data

(60) Provisional application No. 62/403,947, filed on Oct. 4, 2016.

(51) Int. Cl.
*A61M 16/08*    (2006.01)
*A61M 16/06*    (2006.01)
*A61M 25/00*    (2006.01)

(52) U.S. Cl.
CPC .... *A61M 16/0875* (2013.01); *A61M 16/0666* (2013.01); *A61M 16/0683* (2013.01);
(Continued)

(58) Field of Classification Search
CPC ..... A47C 31/123; A61B 1/0058; A61B 1/018; A61B 17/00234; A61B 17/3423;
(Continued)

(56) References Cited

U.S. PATENT DOCUMENTS 7,793,987 B1 * 9/2010 Busch ................ F16L 37/004
285/9.1
7,958,895 B2    6/2011 Nelson
(Continued)

FOREIGN PATENT DOCUMENTS

EP    2039386 A1    3/2009
WO    2004021870 A3    12/2004
(Continued)

*Primary Examiner* — Annette Dixon
(74) *Attorney, Agent, or Firm* — Michael W. Haas

(57) ABSTRACT

A conduit (14A) for conducting a flow of breathing gas from a pressure generating device (4) to a cushion (10) of a patient interface device (8) includes a housing (22) that defines a passage (24) therethrough. The conduit further includes a first magnetic element (30A) disposed on a first side of the passage and a second magnetic element (32A) disposed on a second side of the passage opposite the first side. The first and second magnetic elements are positioned such that the magnetic fields produced by each magnetic element interact in a manner such that the first magnetic element and the second magnetic element are repelled away from each other in a manner which resists collapse of the passage.

20 Claims, 3 Drawing Sheets

(52) U.S. Cl.
CPC .............. *A61M 2025/0059* (2013.01); *A61M 2205/0272* (2013.01)

(58) Field of Classification Search
CPC .......... A61B 2017/00305; A61B 2017/00318; A61B 2017/0034; A61B 2017/3433; A61B 2034/301; A61B 34/30; A61B 5/1076; A61H 2201/0196; A61H 2201/0207; A61H 2201/0228; A61H 2201/1207; A61H 2201/1604; A61H 2201/165; A61H 2205/022; A61M 16/0003; A61M 16/0057; A61M 16/024; A61M 16/06; A61M 16/0605; A61M 16/0622; A61M 16/0633; A61M 16/0666; A61M 16/0683; A61M 16/0816; A61M 16/0875; A61M 16/1055; A61M 16/1075; A61M 16/1095; A61M 16/16; A61M 16/161; A61M 16/20; A61M 16/202; A61M 2016/0021; A61M 2016/0027; A61M 2016/0033; A61M 2025/0024; A61M 2025/0035; A61M 2025/0039; A61M 2025/0058; A61M 2025/0063; A61M 2025/0161; A61M 2025/0915; A61M 2025/09175; A61M 2205/0272; A61M 2205/0283; A61M 2205/15; A61M 2205/332; A61M 2205/3368; A61M 2205/3375; A61M 2205/42; A61M 2205/6054; A61M 2230/62; A61M 25/00; A61M 25/0009; A61M 25/0023; A61M 25/0045; A61M 25/0053; A61M 25/0054; A61M 25/0105; A61M 25/0136; A61M 25/0138; A61M 25/0141; A61M 25/0144; A61M 25/0147; A61M 25/0158; A61M 25/09; A61M 25/1006; E05F 15/42; E05Y 2900/55; F16L 37/004; H01H 2209/002; H01H 3/142; Y10S 310/80; Y10T 29/49826
See application file for complete search history.

(56) References Cited

U.S. PATENT DOCUMENTS

| | | | |
|---|---|---|---|
| 8,146,600 | B2 | 4/2012 | Pflueger |
| 8,297,285 | B2 | 10/2012 | Henry |
| 2004/0054322 | A1* | 3/2004 | Vargas ................ A61B 1/0058 604/95.04 |
| 2004/0070316 | A1* | 4/2004 | Neubauer ............. H01H 3/142 310/330 |
| 2007/0088322 | A1* | 4/2007 | Dicarlo ............ A61M 25/0023 604/523 |
| 2007/0209664 | A1 | 9/2007 | Paraschac |
| 2007/0250036 | A1* | 10/2007 | Volk ................. A61M 25/0158 604/510 |
| 2008/0092904 | A1 | 4/2008 | Gunaratnam |
| 2009/0078259 | A1 | 3/2009 | Kooij |
| 2014/0311492 | A1* | 10/2014 | Stuebiger ......... A61M 16/0683 128/204.23 |
| 2015/0101827 | A1 | 7/2015 | Grashow |
| 2015/0182719 | A1 | 7/2015 | Grashow |
| 2015/0352308 | A1 | 12/2015 | Cullen |

FOREIGN PATENT DOCUMENTS

| | | |
|---|---|---|
| WO | WO2010100639 A1 | 9/2010 |
| WO | WO2011051838 A1 | 5/2011 |
| WO | WO2013123147 A1 | 8/2013 |
| WO | WO2015089270 A1 | 6/2015 |
| WO | WO2015125080 A1 | 8/2015 |

* cited by examiner

US 11,273,279 B2

MAGNETIC ANTI-CRUSH FEATURE FOR CONDUIT

CROSS-REFERENCE TO RELATED APPLICATIONS

This patent application claims the priority benefit under 35 U.S.C. § 371 of international patent application no. PCT/IB2017/056005, filed Sep. 29, 2017, which claims the priority benefit under 35 U.S.C. § 119(e) of U.S. Provisional Application No. 62/403,947 filed on Oct. 4, 2016, the contents of which are herein incorporated by reference.

BACKGROUND OF THE INVENTION

1. Field of the Invention

The present invention pertains to patient interface devices structured to deliver a flow of breathing gas to a user, and, in particular, to a conduit for use in such devices that has a magnetic anti-crush feature.

2. Description of the Related Art

There are numerous situations where it is necessary or desirable to deliver a flow of breathing gas non-invasively to the airway of a patient, i.e., without intubating the patient or surgically inserting a tracheal tube into the patient's esophagus. For example, it is known to ventilate a patient using a technique known as non-invasive ventilation. It is also known to deliver positive airway pressure (PAP) therapy to treat certain medical disorders, the most notable of which is OSA. Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible sealing cushion on the face of a patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

One type of known patient interface device utilizes a headgear which incorporates conduit members or tubes into the headgear that are used to communicate the flow of breathing gas to the interface device. An example arrangement of such a device and headgear is described in U.S. Patent Publication 2015/0182719. In such arrangement, the headgear tubes are constructed from a soft/flexible silicone material which allows the tubes to generally conform to the patient's head for enhanced comfort and fit. Because of such construction, each tube must be large enough to support the entire required airflow since one of the tubes could potentially be completely collapsed when the wearer lays with the side of their head on a pillow.

As many users prefer masks/headgear of minimal size, such large tubes can be undesirable. In order to minimize the size of the headgear tubes in such arrangements, an anti-crush feature can be added to prevent the tube from collapsing under the weight of the head of the wearer such that each tube would only need to be big enough to support one half of the required flow. Two "anti-crush" approaches which have been utilized include (1) headgear tubes constructed from rigid materials, and (2) headgear tubes with internal standoffs (e.g., ribs) that prevent the tube structure from collapsing under the weight of the wearer's head. However, such approaches include undesirable elements. For example, in order to achieve optimal comfort, the headgear tube structure must conform to the shape of the wearer's head. Such existing anti-crush approaches reduce the flexibility of the headgear tubes which results in the tubes being unable to conform to the patients head and thus reduce comfort. In order to reduce the size of the headgear tubes, internal anti-crush features (e.g., ribs) are not desirable as such features not only tend to reduce the conformability of the tubes but also add significant airflow resistance to the tube, thus requiring the size of the tube to be increased to support the required airflow. Internal anti-crush features also contribute to the generation of airflow turbulence within the tube which creates significant noise, which is also undesirable for a wearer.

SUMMARY OF THE INVENTION

In one embodiment, a conduit for conducting a flow of breathing gas from a pressure generating device to a cushion of a patient interface device is provided. The conduit comprises: a housing defining a passage therethrough; a first magnetic element disposed on a first side of the passage; and a second magnetic element disposed on a second side of the passage opposite the first side. The first and second magnetic elements are positioned such that the magnetic fields produced by each magnetic element interact in a manner such that the first magnetic element and the second magnetic element are repelled away from each other in a manner which resists collapse of the passage.

The housing may be formed from a silicone material.

The housing may extend from a first end which is structured to be coupled to the cushion to a second end which is structured to be coupled to a coupling connector.

At least one of the first magnetic element or the second magnetic element may comprise a flexible magnetic element.

The housing may comprise a first arm of a tubing assembly and the conduit may further comprise a second arm comprising: a second housing defining a second passage therethrough. The second housing extends from the second end of the housing of the first arm to another end, which is structured to be coupled to the cushion. A third magnetic element is disposed on a first side of the second passage, and a fourth magnetic element is disposed on a second side of the second passage opposite the first side of the second passage. The third and fourth magnetic elements are positioned such that the magnetic fields produced by each magnetic element interact in a manner such that the third magnetic element and the fourth magnetic element are repelled away from each other, thus resisting collapse of the second passage.

The housing may be a portion of a tubing assembly structured to secure the cushion to the head of a patient.

One or both of the first magnetic element and the second magnetic element may comprise a plurality of discrete magnetic elements.

In another embodiment, a tubing assembly for use in delivering a flow of breathing gas to a cushion is provided. The tubing assembly comprises a housing having a portion structured to be coupled to a coupling connector for receiving a flow of breathing gas from a pressure generating device. The housing comprises a first arm extending from a first side of the portion of the housing and a second arm extending from a second side of the housing opposite the first side. Each arm comprises: a housing defining a passage therethrough. A first magnetic element is disposed on a first side of the passage; and a second magnetic element disposed on a second side of the passage opposite the first side. The first and second magnetic elements are positioned such that the magnetic fields produced by each magnetic element interact in a manner such that the first magnetic element and the second magnetic element are repelled away from each other in a manner that resists collapse of the passage.

The first arm may extend from the portion to a first end which is structured to engage the cushion, and the second arm may extend from the portion to a second end which is structured to engage the cushion.

At least one of the first magnetic element or the second magnetic element may comprise a flexible magnetic element.

The housing of each arm may comprise a portion of a single integral housing.

The integral housing may be formed from a silicone material.

In yet another embodiment, a patient interface device comprises: a cushion and a tubing assembly, the tubing assembly comprising a housing having a portion structured to be coupled to a coupling connector for receiving a flow of breathing gas from a pressure generating device. The housing comprises: a first arm extending from a first side of the portion of the housing to a first end which is coupled to the cushion, and a second arm extending from a second side of the housing opposite the first side to a second end which is coupled to the cushion. Each arm comprises: a housing defining a passage therethrough; a first magnetic element disposed on a first side of the passage; and a second magnetic element disposed on a second side of the passage opposite the first side. The first and second magnetic elements are positioned such that the magnetic fields produced by each magnetic element interact in a manner such that the first magnetic element and the second magnetic element are repelled away from each other in a manner that resists collapse of the passage.

The first end of the first arm may be coupled to a first end of the cushion and the second end of the second arm may be coupled to a second end of the cushion opposite the first end of the cushion.

At least one of the first magnetic element or the second magnetic element may comprise a flexible magnetic element.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
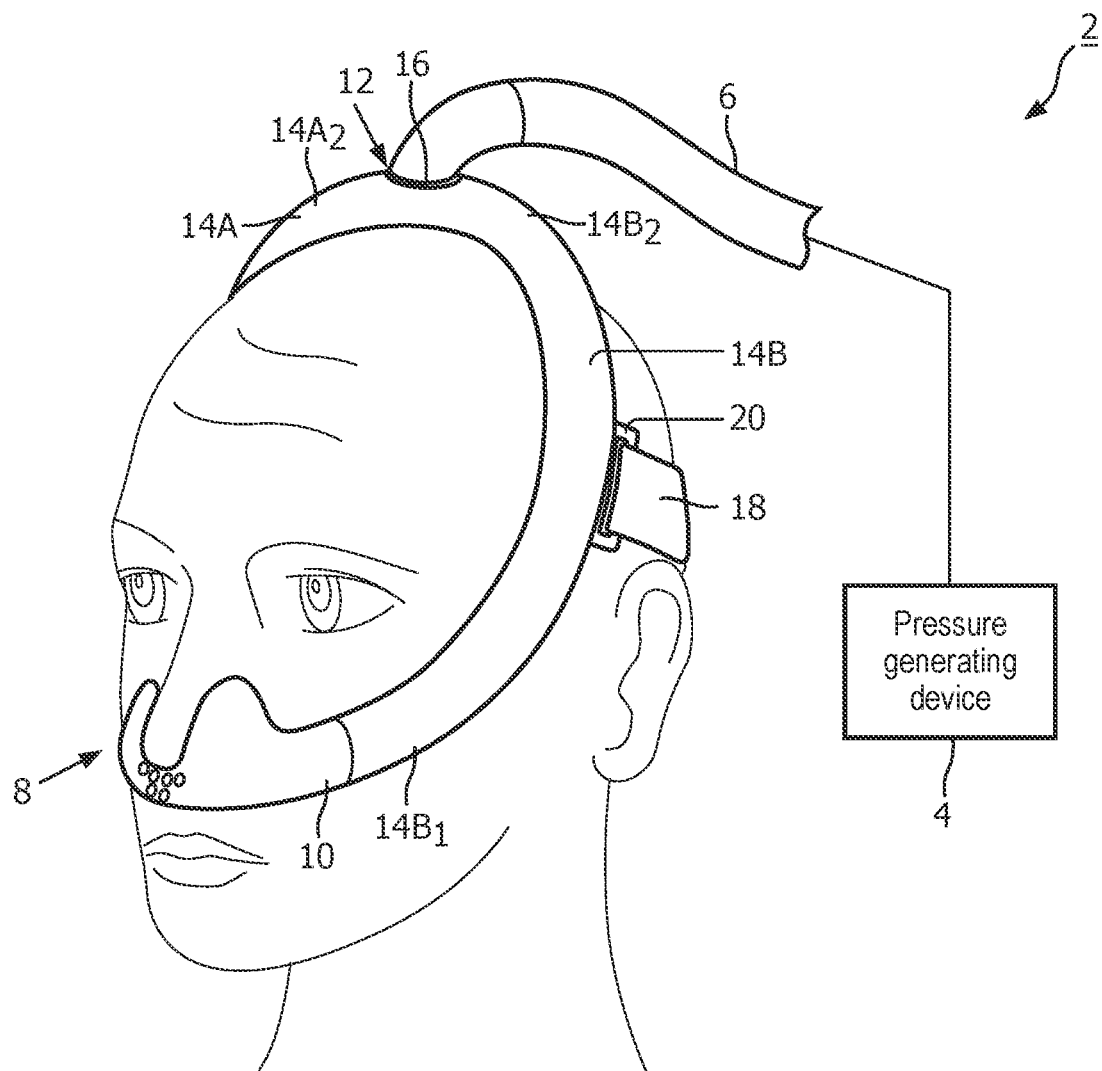
FIG. 1 is a schematic diagram of a system adapted to provide a regimen of respiratory therapy to a patient according to one exemplary embodiment of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 2 adapted to provide a regimen of respiratory therapy to a patient according to one exemplary embodiment of the invention is generally shown in FIG. 1. System 2 includes a pressure generating device 4, a delivery conduit 6, and a patient interface device 8. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8.

In the exemplary embodiment, patient interface device 8 comprises a cradle style nasal mask structured to engage the nose of the patient and provide a seal against the surfaces of the nasal septum and nostrils (and possibly the portion of the patient's mouth above the upper lip) as described in detail herein. In the present embodiment, patient interface device 8 includes a cradle style sealing cushion 10 coupled to a tubing assembly 12. In an example embodiment of the present invention, tubing assembly 12 is formed as a unitary member from a silicone material. Such arrangement provides for tubing assembly 12 to readily conform to a patient's head while also minimizing locations for potential leaks.

As seen in FIG. 1, tubing assembly 12 includes a first arm 14A structured to rest along a first side of the patient's head and a second arm 14B structured to rest along an opposite second side of the patient's head when patient interface device 8 is donned by the patient. A first end $14A_1$ (see FIG. 2) of first arm 14A and a first end $14B_1$ of second arm 14B are each fluidly coupled to cradle style sealing cushion 10 such that sealing cushion 10 is secured to the head of the patient via tubing assembly 12. A second end $14A_2$ of first arm 14A and a second end $14B_2$ of second arm 14B are each fluidly coupled to a coupling connector 16 structured to rest on top of the head of the patient when patient interface device 8 is donned by the patient. Delivery conduit 6 is fluidly coupled to coupling connector 16 to allow the flow of breathing gas from pressure generating device 4 to be communicated to cradle style sealing cushion 10 through tubing assembly 12, and then, to the airway of a patient. Accordingly, each of first and second arms 14A and 14B act as a conduit for conducting a flow of breathing gas from pressure generating device 4 to cushion 10. Straps 18 of a headgear component are attached to first arm 14A and second arm 14B via attachment members 20 to secure patient interface device 8 to the patient's head.

Figure 2:
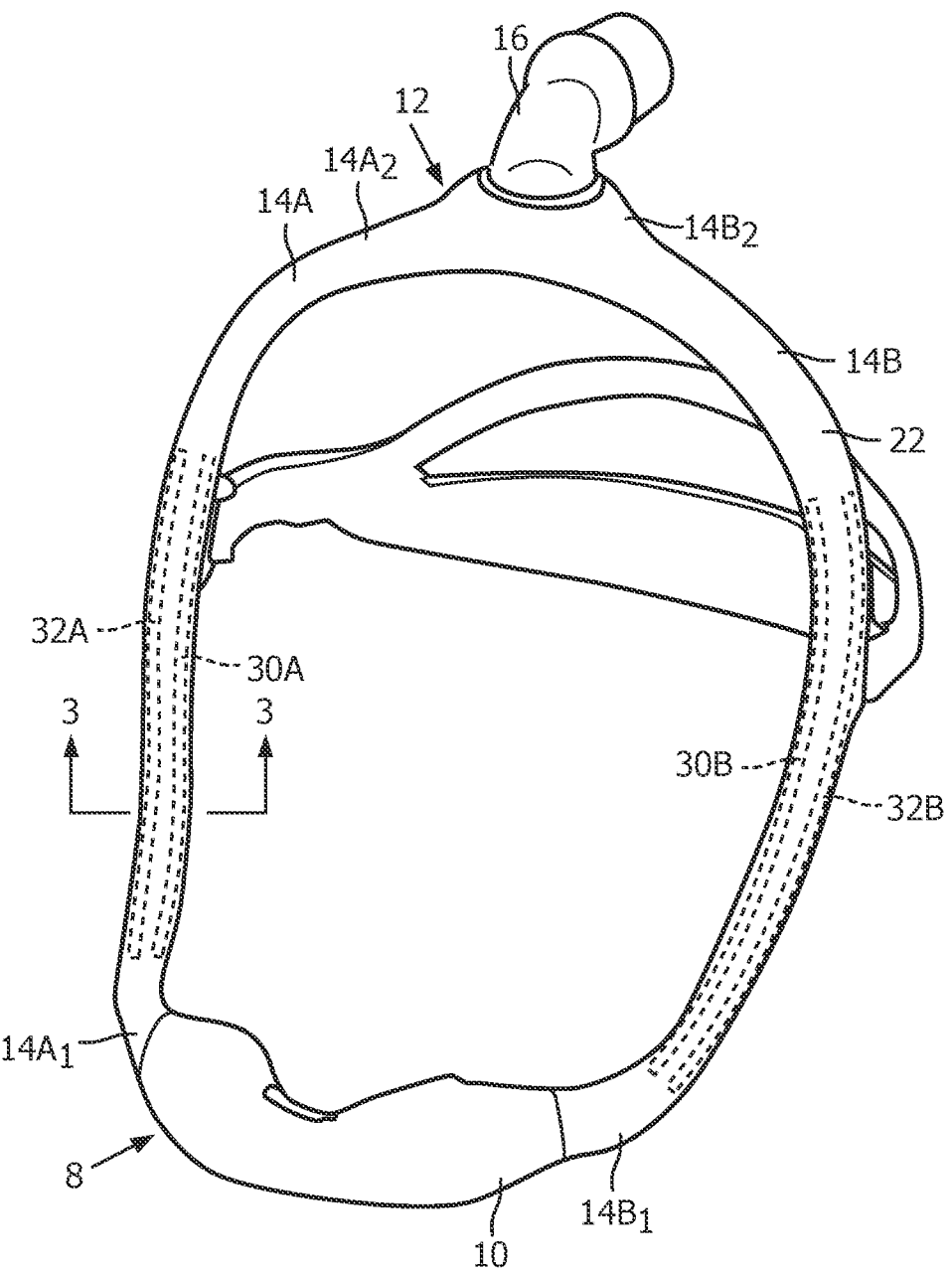
FIG. 2 is a partially schematic front isometric view of the patient interface device of the system of FIG. 1.
Figure 3:
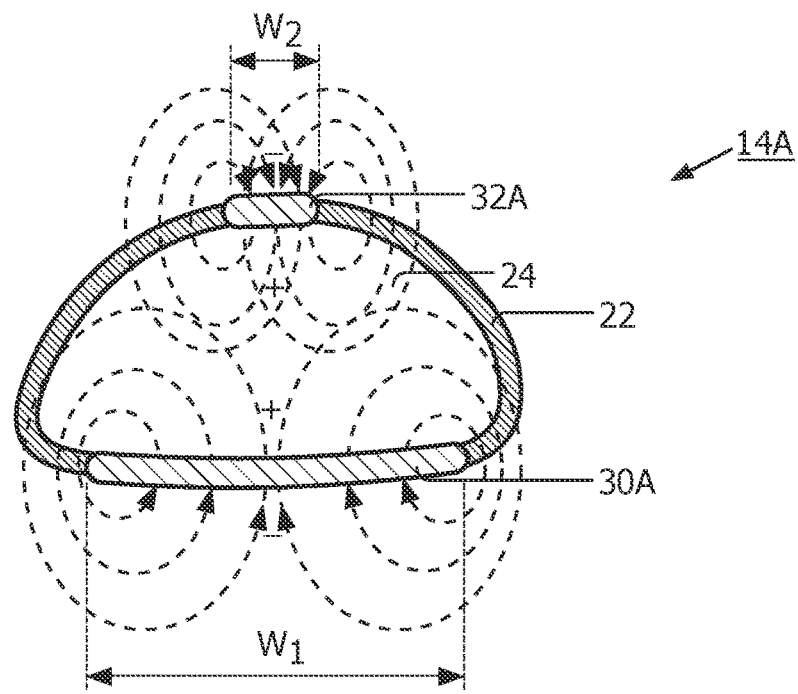
FIG. 3 is a sectional view of a portion of the tubing assembly of the patient interface device of FIG. 2 taken along line 3-3 of FIG. 2.
Figure 4:
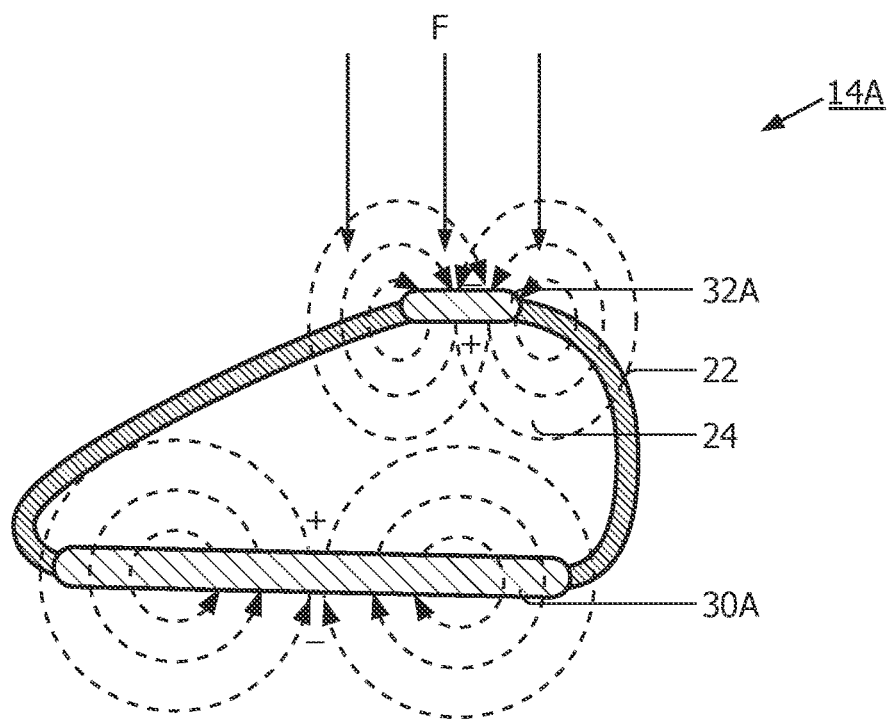
FIG. 4 is another version of the sectional view of FIG. 3 shown in a distorted state resulting from the application of an external force.

Referring now to FIGS. 2-4, each of first and second arms 14A and 14B of tubing assembly 12 includes a housing 22 which defines a passage 24 (FIGS. 3 and 4) therethrough through which a flow of breathing gas is conducted. As shown in FIG. 2, each of first and second arms 14A and 14B also includes a first magnetic element 30A, 30B (shown schematically in dashed line) disposed on or in the patient facing side of arms 14A, 14B as well as a second magnetic element 32A, 32B (shown schematically in dashed line) disposed on or in the side of arms 14A, 14B which faces away from the patient. As shown in the sectional view of first arm 14A shown in FIGS. 3 and 4, first magnetic element 30A and second magnetic element 32A are positioned such that the magnetic fields (shown schematically in dashed lines) produced by each magnetic element 30A, 32A interact in a manner such that magnetic elements 30A, 32A are repelled away from each other, thus resisting collapse of first arm 14A and keeping passage 24 open when an external force, such as force F shown in FIG. 4, is applied to housing 22.

Continuing to refer to FIGS. 3 and 4, in order to keep first and second magnetic elements 30A and 32A from tending to reorient themselves (i.e., to attempt to move so as to attract toward each other), magnetic elements 30A and 32A may be of different dimensions. In the example embodiment illustrated in FIGS. 3 and 4, first magnetic element 30A is of a greater width $W_1$ (when viewed in cross-section perpendicular to passage 24) than the width $W_2$ of second magnetic element. Although shown with $W_1$ being greater than $W_2$, it is to be appreciated that $W_2$ could be greater than $W_1$ without varying from the scope of the present invention. Additionally, $W_1$ and $W_2$ may be equal in length (as measured parallel to passage 24), with the general structure of housing 22 used to inhibit magnetic elements 30A and 32A from changing orientation.

Although not described in particular detail herein, it is to be appreciated that magnetic elements 30B and 32B of second arm 14B are arranged in a similar manner as elements 30A and 32A described for first arm 14A so as to keep the passage defined within second arm 14B from collapsing.

Although shown as having both positive poles generally facing each other in the example depicted in FIG. 3, it is to be appreciated that each of magnetic elements 30A and 32A could be also be positioned such that there negative poles are facing each other without varying from the scope of the present concept.

Although shown generally as continuous elements in FIG. 2, it is to be appreciated that any of magnetic elements 30A, 30B, 32A and 32B may also comprise a plurality of discrete magnetic elements which are disposed in a predetermined manner. In either case, magnetic elements 30A, 30B, 32A and 32B are positioned and structured to allow for each of first arm 14A and second arm 14B to readily conform to the patient. Examples of suitable magnetic elements include, for example, without limitation, permanent magnets such as ferrite, ceramic, neodymium iron boron, samarium cobalt or electromagnets. Flexible magnets such as, for example, without limitation, magnetic powders bonded to elastomers or other flexible magnets comprising magnetic nanoparticles may also be employed to maintain conformability and comfort of the headgear without varying from the scope of the present invention.

It is also to be appreciated that the positioning of magnetic elements 30A, 30B, 32A and 32B along the length of either of first arm 14A or second side arm 14B may be varied without varying from the scope of the present invention. For example, such opposing magnetic elements may be provided only at one or more particular points of concern (e.g., without limitation, near the cheekbone of a patient, side of head, etc.) or generally along the entire length thereof.

From the foregoing description is can be readily appreciated that embodiments of the present invention provide a magnetic anti-crush feature which acts to keep a conduit used in communicating a flow of breathing gas from collapsing. Such solution does not require any structures within the conduit and thus does not adversely affect flow of the breathing gas or create additional noise. Such solution also does not adversely affect the flexibility of the conduit.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A conduit for conducting a flow of breathing gas from a pressure generating device to a cushion of a patient interface device, the conduit comprising:
a housing defining a passage therethrough;
a first magnetic element disposed on a first side of the passage; and
a second magnetic element disposed on a second side of the passage opposite the first side, wherein the first and second magnetic elements are positioned such that the magnetic fields produced by each magnetic element interact in a manner such that the first magnetic element and the second magnetic element are repelled away from each other in a manner that resists collapse of the passage.

2. The conduit of claim 1, wherein the housing extends from a first end which is structured to be coupled to the cushion to a second end which is structured to be coupled to a coupling connector.

3. The conduit of claim 2, wherein the housing comprises a first arm of a tubing assembly, and wherein the conduit further comprises a second arm comprising:
a second housing defining a second passage therethrough, the second housing extending from the second end of the housing of the first arm to another end which is structured to be coupled to the cushion;
a third magnetic element disposed on a first side of the second passage; and
a fourth magnetic element disposed on a second side of the second passage opposite the first side of the second passage, wherein the third and fourth magnetic elements are positioned such that the magnetic fields produced by each magnetic element interact in a manner such that the third magnetic element and the fourth magnetic element are repelled away from each other, thus resisting collapse of the second passage.

4. The conduit of claim 1, wherein, when viewed in a cross section perpendicular to the passage, the first magnetic element has a first width, and
the second magnetic element has a second width different than the first width.

5. The conduit of claim 4, wherein the second width is less than the first width.

6. The conduit of claim 1, wherein the housing is formed from a silicone material.

7. The conduit of claim 1, wherein at least one of the first magnetic element or the second magnetic element comprises a flexible magnetic element.

8. The conduit of claim 1, wherein the housing is a portion of a tubing assembly structured to secure the cushion to the head of a patient.

9. The conduit of claim 1, wherein one or both of the first magnetic element and the second magnetic element comprises a plurality of discrete magnetic elements.

10. The conduit of claim 1, wherein at least one of the first magnetic element and/or the second magnetic element is a unitary magnet substantially extending the longitudinal length of the passage.

11. A tubing assembly for use in delivering a flow of breathing gas to a cushion, the tubing assembly comprising a housing having a portion structured to be coupled to a coupling connector for receiving a flow of breathing gas from a pressure generating device, the housing comprising a first arm extending from a first side of the portion of the housing and a second arm extending from a second side of the housing opposite the first side, wherein each arm comprises:
a housing defining a passage therethrough;
a first magnetic element disposed on a first side of the passage; and
a second magnetic element disposed on a second side of the passage opposite the first side, wherein the first and second magnetic elements are positioned such that the magnetic fields produced by each magnetic element interact in a manner such that the first magnetic element and the second magnetic element are repelled away from each other, thus resisting collapse of the passage.

12. The tubing assembly of claim 11, wherein the housing of each arm comprises a portion of a single integral housing.

13. The tubing assembly of claim 12, wherein the integral housing is formed from a silicone material.

14. The tubing assembly of claim 11, wherein the first arm extends from the portion to a first end which is structured to engage the cushion, and wherein the second arm extends from the portion to a second end which is structured to engage the cushion.

15. The tubing assembly of claim 11, wherein at least one of the first magnetic element or the second magnetic element comprises a flexible magnetic element.

16. The tubing assembly of claim 11, wherein, when viewed in a cross section perpendicular to the passage, the first magnetic element has a first width, and
the second magnetic element has a second width different than the first width.

17. The tubing assembly of claim 11, wherein the second width is less than the first width.

18. A patient interface device comprising:
a cushion; and
a tubing assembly, the tubing assembly comprising a housing having a portion structured to be coupled to a coupling connector for receiving a flow of breathing gas from a pressure generating device, the housing comprising:
a first arm extending from a first side of the portion of the housing to a first end which is coupled to the cushion, and
a second arm extending from a second side of the housing opposite the first side to a second end which is coupled to the cushion, wherein each arm comprises:
a housing defining a passage therethrough;
a first magnetic element disposed on a first side of the passage; and
a second magnetic element disposed on a second side of the passage opposite the first side, wherein the first and second magnetic elements are positioned such that the magnetic fields produced by each magnetic element interact in a manner such that the first magnetic element and the second magnetic element are repelled away from each other, thus resisting collapse of the passage.

19. The patient interface device of claim 18, wherein the first end of the first arm is coupled to a first end of the cushion and wherein the second end of the second arm is coupled to a second end of the cushion opposite the first end of the cushion.

20. The patient interface device of claim 18, wherein at least one of the first magnetic element or the second magnetic element comprises a flexible magnetic element.

* * * * *